(12) United States Patent
Deladi et al.

(10) Patent No.: US 10,405,828 B2
(45) Date of Patent: Sep. 10, 2019

(54) LOCATION DETERMINATION APPARATUS

(75) Inventors: Szabolcs Deladi, Veldhoven (NL); Erik Godefridus Antonius Harks, Eindhoven (NL); Ameet Kumar Jain, New York, NY (US); Francois Guy Gerard Marie Vignon, Croton-on-Hudson, NY (US); Maikel Hendriks, Eindhoven (NL); Garardus Henricus Maria Gijsbers, Liempde (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 450 days.

(21) Appl. No.: 13/885,016

(22) PCT Filed: Oct. 18, 2011

(86) PCT No.: PCT/IB2011/054617
§ 371 (c)(1),
(2), (4) Date: May 13, 2013

(87) PCT Pub. No.: WO2012/066437
PCT Pub. Date: May 24, 2012

(65) Prior Publication Data
US 2013/0245433 A1    Sep. 19, 2013

Related U.S. Application Data

(60) Provisional application No. 61/472,721, filed on Apr. 7, 2011.

(51) Int. Cl.
*A61B 5/00* (2006.01)
*A61B 8/00* (2006.01)
(Continued)

(52) U.S. Cl.
CPC ......... *A61B 8/4483* (2013.01); *A61B 8/0883* (2013.01); *A61B 8/12* (2013.01);
(Continued)

(58) Field of Classification Search
CPC .............................................. A61B 2019/5276
(Continued)

(56) References Cited

U.S. PATENT DOCUMENTS 5,515,853 A * 5/1996 Smith et al. .................. 600/437
5,655,276 A   8/1997 Pattanayak et al.
(Continued)

FOREIGN PATENT DOCUMENTS

CN   1168625 A   12/1997
EP   1034738     9/2000
(Continued)

OTHER PUBLICATIONS

D.N. Stephens, et al., "The Acoustic Lens Design and in Vivo Use of a Multifunctional Catheter Combining Intracardiac Ultrasound Imaging and Electrophysiology Sensing", IEEE Tran. Ultrasonics, Ferroelectrics & Freq. Control, 55 (3), Mar. 2008, pp. 602-618.

*Primary Examiner* — Rajeev P Siripurapu

(57) ABSTRACT

The invention relates to location determination apparatus for determining a location of a first object (2) like a catheter within a second object (3) being, for example, the heart of a person. The first object comprises a first ultrasound unit, and a second ultrasound unit (5) is located outside the second object. A location determination unit determines the location of the first object within the second object based on ultrasound signals transmitted 5 between the first ultrasound unit and the second ultrasound unit. This allows determining the location of the first object within the second object reliably in a way which is an alternative to using a transmission of electrical signals for determining the location and (Continued)

which may lead to an improved accuracy of determining the location.

12 Claims, 7 Drawing Sheets

(51) Int. Cl.
| | | |
|---|---|---|
| *A61B 8/08* | (2006.01) | |
| *A61B 8/12* | (2006.01) | |
| *B06B 1/06* | (2006.01) | |
| *A61B 34/20* | (2016.01) | |
| *A61B 18/14* | (2006.01) | |
| *A61B 18/00* | (2006.01) | |
| *G01S 15/46* | (2006.01) | |
| *A61B 90/00* | (2016.01) | |

(52) U.S. Cl.
CPC .............. *A61B 8/445* (2013.01); *A61B 34/20* (2016.02); *B06B 1/0629* (2013.01); *A61B 18/1492* (2013.01); *A61B 2018/00738* (2013.01); *A61B 2018/00839* (2013.01); *A61B 2034/2051* (2016.02); *A61B 2034/2063* (2016.02); *A61B 2090/364* (2016.02); *A61B 2090/3782* (2016.02); *G01S 2015/465* (2013.01); *Y10T 29/42* (2015.01)

(58) Field of Classification Search
USPC ........................................................ 600/424
See application file for complete search history.

(56) References Cited

U.S. PATENT DOCUMENTS

| | | | |
|---|---|---|---|
| 5,684,884 A | 11/1997 | Nakaya et al. | |
| 6,298,261 B1 | 10/2001 | Rex | |
| 6,311,000 B1 | 10/2001 | Schneider | |
| 6,476,541 B1 | 11/2002 | Smith et al. | |
| 6,806,622 B1 | 10/2004 | Schmidt et al. | |
| 6,896,657 B2 | 5/2005 | Willis | |
| 7,573,181 B2 | 8/2009 | Rhim et al. | |
| 7,575,550 B1* | 8/2009 | Govari | 600/437 |
| 7,604,601 B2 | 10/2009 | Altmann et al. | |
| 7,846,101 B2 | 12/2010 | Eberle et al. | |
| 8,475,524 B2 | 7/2013 | Schwartz | |
| 9,901,321 B2 | 2/2018 | Harks et al. | |
| 2002/0107445 A1 | 8/2002 | Govari | |
| 2002/0153805 A1 | 10/2002 | Smith et al. | |
| 2003/0093067 A1 | 5/2003 | Panescu | |
| 2004/0049121 A1* | 3/2004 | Yaron | 600/544 |
| 2004/0215079 A1 | 10/2004 | Omura et al. | |
| 2005/0156491 A1 | 7/2005 | Scott | |
| 2006/0253032 A1* | 11/2006 | Altmann et al. | 600/466 |
| 2007/0049821 A1 | 3/2007 | Willis | |
| 2007/0106147 A1 | 5/2007 | Altmann et al. | |
| 2009/0015109 A1 | 1/2009 | Schuh | |
| 2009/0034370 A1 | 2/2009 | Guo | |
| 2009/0264767 A1 | 10/2009 | Griffin et al. | |
| 2010/0198065 A1 | 8/2010 | Thapliyal et al. | |

FOREIGN PATENT DOCUMENTS

| | | |
|---|---|---|
| EP | 1362553 | 11/2003 |
| EP | 1749475 | 2/2007 |
| EP | 2210563 | 7/2010 |
| GB | 2331365 | 5/1999 |
| JP | 2001200256 A | 7/2001 |
| JP | 2001200256 A | 10/2001 |
| JP | 2006025960 A | 2/2006 |
| JP | 2006280591 A | 10/2006 |
| WO | WO2010082146 | 7/2010 |

* cited by examiner 65  66

LOCATION DETERMINATION APPARATUS

FIELD OF THE INVENTION

The invention relates to a location determination apparatus, a location determination method and a location determination computer program for determining a location of a first object within a second object, in particular, for determining the location of an in-body device like a catheter or a needle within a heart of a person.

BACKGROUND OF THE INVENTION

U.S. Pat. No. 7,604,601 B2 discloses a medical imaging system for imaging a patient's body. The medical imaging system includes a catheter having a position sensor and an ultrasound imaging sensor, wherein the position sensor emits electrical signals indicative of positional information of a portion of the catheter in the patient's body, and the ultrasound imaging sensor emits ultrasound energy to a target in the patient's body, receives ultrasound echoes reflected from the target in the patient's body and emits signals relating to the ultrasound echoes reflected from the target in the patient's body. A position processor is operatively connected to the catheter for determining positional information of the portion of the catheter based on the electrical signals emitted by the position sensor. The system further includes a display and an image processor operatively connected to the catheter, the position processor and the display. The image processor displays on the display a catheter icon in a same orientation as an orientation of the portion of the catheter in the patient's body based on the positional information derived from the position sensor. The image processor also generates an ultrasound image of the target based on the signals emitted by the ultrasound sensor and depicts in real-time the generated ultrasound image on the display in the same orientation as the orientation of the portion of the catheter in the patient's body. The positional information of the portion of the catheter, which is based on the electrical signals emitted by the position sensor, can have a relatively low accuracy, which may lead to an inaccurate positioning of the catheter within the patient's body.

SUMMARY OF THE INVENTION

It is an object of the present invention to provide a location determination apparatus for providing an alternative way of determining a location of a first object within a second object, in particular, of determining a location of an in-body device within a heart of a person, which may lead to an improved accuracy of determining the location.

In a first aspect of the present invention a location determination apparatus for determining a location of a first object within a second object is presented, wherein the location determination apparatus comprises:
  the first object comprising a first ultrasound unit,
  a second ultrasound unit for being located outside the second object, wherein the first ultrasound unit and the second ultrasound unit are adapted to transmit ultrasound signals between them,
  a location determination unit for determining the location of the first object within the second object based on the transmitted ultrasound signals.

Since the ultrasound signals are transmitted between first and second ultrasound units, wherein the first ultrasound unit is comprised by the first object and the second ultrasound unit is located outside of the second object, and since the location of the first object within the second object is determined based on the transmitted ultrasound signals, the location of the first object within the second object can reliably be determined in an alternative way, i.e. without necessarily relying on electric signals emitted by a position sensor, which may lead to an improved accuracy of determining the location. The first object is preferentially an in-body device like a catheter, in particular, a catheter tip, and the second object is preferentially a part of a person or of an animal like an organ, in particular, the heart. For example, a catheter tip can be equipped with the first ultrasound unit and the second ultrasound unit can be located outside of the heart, for example, arranged on the thorax of the person.

That the first ultrasound unit and the second ultrasound unit are adapted to transmit ultrasound signals between them, means that the first ultrasound unit can emit ultrasound signals, which are received by the second ultrasound unit, or that the second ultrasound unit can emit ultrasound signals, which are received by the first ultrasound unit.

At least one of the first ultrasound unit and the second ultrasound unit can comprise several ultrasound transducers for transmitting ultrasound signals between the first and second ultrasound units. For example, the first ultrasound unit may comprise various ultrasound transducers positioned on the surface of the first object.

In particular, at least one of the first ultrasound unit and the second ultrasound unit can comprise several ultrasound transducers for transmitting ultrasound signals between the first and second ultrasound units, wherein the several ultrasound transducers emit ultrasound signals at the same or at different frequencies. Preferentially, the first ultrasound unit comprises several ultrasound transducers arranged at positions on or within the first object, which are known with respect to the first object, wherein the several ultrasound transducers emit or receive ultrasound signals at different frequencies for transmitting ultrasound signals between the several ultrasound transducers and the second ultrasound unit at different frequencies, and wherein the location determination unit is adapted to determine the orientation of the first object based on the transmitted ultrasound signals and the positions of the several ultrasound transducers, which are known with respect to the first object. In particular, the location determination unit can be adapted to determine first positions being the positions of the several ultrasound transducers on the first object with respect to the second ultrasound unit and to determine the orientation of the first object with respect to the second ultrasound unit based on the determined first positions and second positions being the positions of the several ultrasound transducers, which are known with respect to the first object. The location determination unit can therefore be adapted to determine not only the position, but also the orientation of, for example, a catheter tip.

Preferentially, adjacent frequencies are separated by at least the sum of half the bandwidth of the ultrasound transducers with the adjacent frequencies, wherein the bandwidth is preferentially defined as the half width at half maximum. This allows a clear separation of adjacent frequencies.

The several ultrasound transducers can emit ultrasound signals simultaneously or alternately.

In an embodiment, at least one of the first ultrasound unit and the second ultrasound unit comprises one or several two- or three-dimensional ultrasound transducers. In particular, preferentially the first object, which is preferentially an in-body device like a catheter, comprises several ultrasound transducers, which emit ultrasound simultaneously or alternately at the same or different frequencies, and the second ultrasound unit comprises preferentially one or several two- or three-dimensional ultrasound transducers for receiving the emitted ultrasound. Alternatively, also the second ultrasound unit can emit ultrasound and the first ultrasound unit can receive the ultrasound.

The three-dimensional ultrasound transducer is, for example, a broadband external array of sub-ultrasound transducers, which can be used for three-dimensional trans thoracic echography (TTE), or a natural orifice translumenal (NOT) three-dimensional ultrasound transducer, which can be used for three-dimensional trans esophageal echography (TEE). The three-dimensional ultrasound transducer can also be of other shape and/or size.

It is also preferred that the location determination unit is adapted to determine the location of the first object within the second object based on at least one of the time of flight and the transmission direction of the transmitted ultrasound signals. For example, the position of a catheter can be determined by the time of flight and a directionality of the one or several ultrasound transducers on the catheter with respect to the external one or several ultrasound transducers being outside of the heart.

In a preferred embodiment, the first object is adapted to measure a property of the second object at the location at which the first object is arranged within the second object. For example, the first object can be a catheter comprising a sensing electrode at the tip of the catheter for picking up electrical activation signals at a location that has been determined by the location determination unit. It is also preferred that the location determination apparatus comprises a map determination unit for determining a property map based on determined locations of the first object within the second object and properties of the second object, which have been measured at the determined locations. In particular, the map determination unit can be adapted to determine an electroanatomic map based on electrical activation signals measured at positions determined by the location determination unit. For instance, a catheter tip comprising a sensing electrode can be moved to different positions on the heart wall, wherein the different positions can be determined by the location determination unit, and wherein electrical activation signals can be measured at these locations and used to generate an electroanatomic map. This allows generating an electroanatomic map accurately.

It is further preferred that the first object is adapted to apply energy to the second object at the location at which the first object is arranged within the second object. For example, the first object can be a catheter comprising an ablation element like an ablation electrode for ablating the second object, in particular, a heart of a person or of an animal. This allows applying energy to the second object at a desired location determined by the location determination unit.

Preferentially, the map determination unit is further adapted to determine an energy application map based on determined locations of the first object within the second object, at which energy has been applied. In particular, the map determination unit can be adapted to determine an anatomic map showing the anatomical positions at which energy has been applied, in particular, at which cardiac tissue has been ablated. Also properties like electrical properties measured by a sensing electrode and/or positions at which energy shall be applied can be shown in the anatomic map. The map can therefore be a combined map showing positions at which energy has been applied and/or is to be applied and positions at which a property of the second object has been sensed, wherein at the latter positions the sensed property can be shown.

The location determination unit is preferentially adapted to determine the location of the first object within the second object with respect to the position of the second ultrasound unit. The position of the second ultrasound unit can be known with respect to a reference coordinate system, in order to determine the location of the first object within the second object with respect to the reference coordinate system.

In an embodiment, the location determination apparatus comprises a fixation arrangement for fixing the second ultrasound unit on a subject in which the second object is located. The fixation arrangement is, for example, a frame or robot, on which the second ultrasound unit is mounted, in order to keep the second ultrasound unit, in particular, ultrasound transducers of the second ultrasound unit, fixed onto the subject, which is preferentially the body of a person. The frame or robot can be a stereotactic frame or robot. The fixation arrangement can also be a vest, in which the second ultrasound unit is embedded and which can be worn by a person. By using the fixation arrangement the location determination apparatus can be operated, while the second ultrasound unit does not change its position. For example, if the first object is adapted to apply energy to the second object, in particular, if the first object is an ablation catheter for performing a cardiac arrhythmia treatment, this application of energy can be performed under ultrasound guidance, while the second ultrasound unit does not change its position or while possible movements of the second ultrasound unit are at least reduced. The fixation arrangement can define a reference coordinate system, wherein the position of the second ultrasound unit, in particular, the positions of a ultrasound transducers of the second ultrasound unit, is known with respect to the reference coordinate system and wherein the location determination unit can determine the location of the first object within the second object with respect to the reference coordinate system.

In an embodiment, the location determination apparatus further comprises a second ultrasound unit position determination unit for determining the position of the second ultrasound unit with respect to a reference coordinate system, wherein the location determination unit is adapted to determine the position of the first object within the second object with respect to the reference coordinate system based on the transmitted ultrasound signals and the determined position of the second ultrasound unit with respect to the reference coordinate system. In this embodiment, energy can be accurately applied to desired locations within the second object and/or properties can be accurately sensed at desired locations within the second object, even if the second ultrasound unit, in particular, ultrasound transducers of the second ultrasound unit, changes the position during the respective procedure.

The second ultrasound unit position determination unit can comprise three-dimensional position sensors like electro-magnetic (EM), optical or fiber shape sensors, which are attached to the second ultrasound unit, in particular, to the ultrasound transducers of the second ultrasound unit, and which may continuously measure the position of the second ultrasound unit.

It is further preferred that location determination apparatus comprises an ultrasound image generation unit for generating an ultrasound image of the second object based on ultrasound information from at least one of the first ultrasound unit and the second ultrasound unit, wherein the location determination unit is adapted to determine the location of the first object within the second object with respect to the ultrasound image based on the ultrasound signals transmitted between the first and second ultrasound units and the ultrasound information. In a preferred embodiment, the location determination apparatus further comprises a registration unit for registering the ultrasound image with a previously acquired image or a model of the second object, wherein the location determination unit is adapted to determine the location of the first object within the second object based on the determined location with respect to the ultrasound image and the registration result. The ultrasound image of the second object is preferentially a currently acquired three-dimensional ultrasound image and the previously acquired image is preferentially a previously acquired three-dimensional image of the same or another imaging modality like an ultrasound image, a computed tomography image, a magnetic resonance image, et cetera. The model is also preferentially three-dimensional. The location determination apparatus is preferentially adapted to determine the location of the first object within the second object shown in the previously acquired image or by the model. In an embodiment, the ultrasound image can be generated in real-time during an interventional procedure, wherein previously acquired image or model of, for example, the heart, can be registered with the real-time ultrasound image, in order to allow the location determination apparatus to determine the location of the first object within the second object based on the determined location with respect to the ultrasound image and the registration result in real-time. In particular, the location of, for example, a catheter tip or needle tip can be shown in real-time on a previously acquired image or model of, for example, the heart.

In a further aspect of the present invention a location determination method for determining a location of a first object within a second object is presented, wherein the location determination method comprises:
  transmitting ultrasound signals between a first ultrasound unit comprised by the first object and a second ultrasound unit located outside the second object, and
  determining the location of the first object within the second object based on the transmitted ultrasound signals by a location determination unit.

In a further aspect of the present invention a location determination computer program for determining the location of a first object within a second object is presented, wherein the location determination computer program comprises program code means for causing a location determination apparatus as defined in claim 1 to carry out the steps of the location determination method as defined in claim 12, when the location determination computer program is run on a computer controlling the location determination apparatus.

It shall be understood that the location determination apparatus of claim 1, the location determination method of claim 12, and the location determination computer program of claim 13 have similar and/or identical preferred embodiments, in particular, as defined in the dependent claims.

It shall be understood that a preferred embodiment of the invention can also be any combination of the dependent claims with the respective independent claims.

These and other aspects of the invention will be apparent from and elucidated with reference to the embodiments described hereinafter.

DETAILED DESCRIPTION OF EMBODIMENTS

Figure 1:
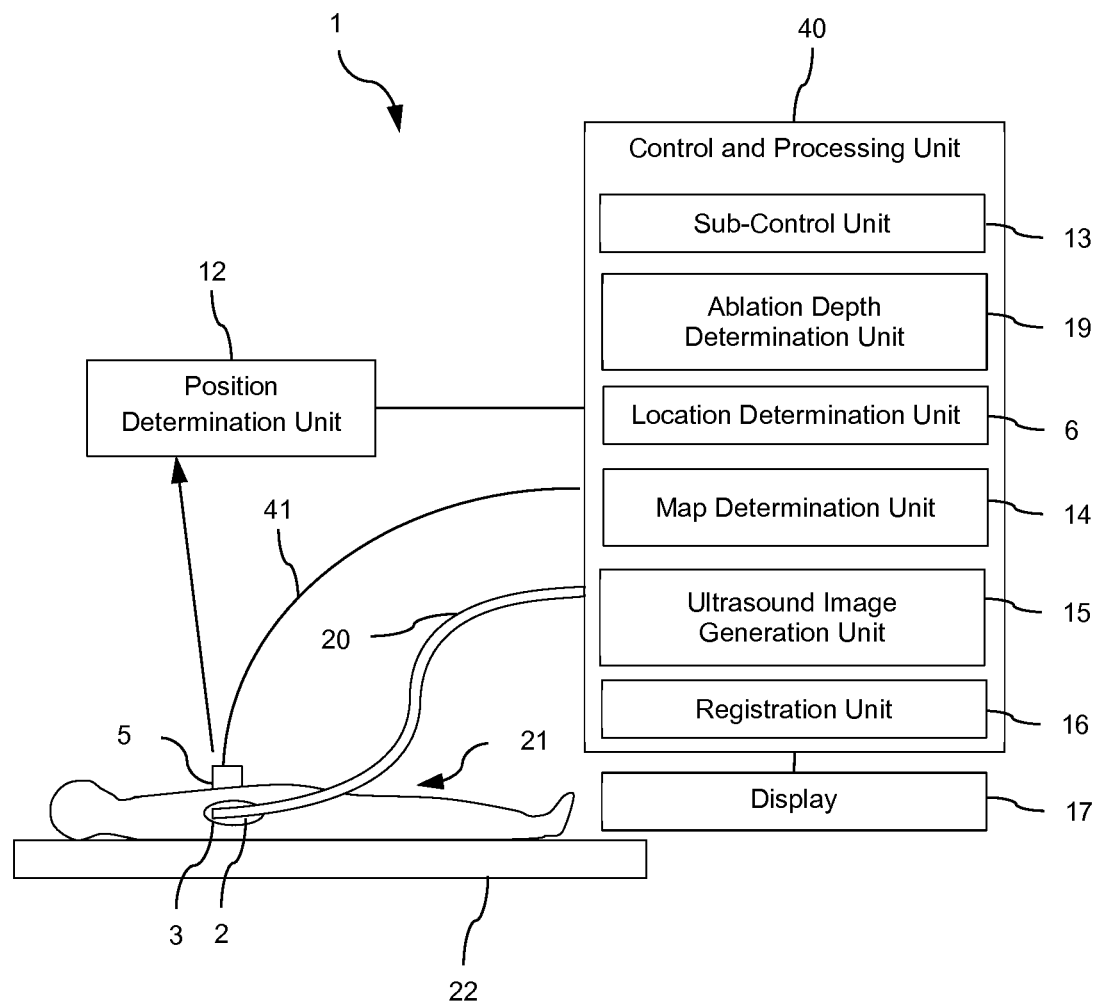
FIG. 1 shows schematically and exemplarily an embodiment of a location determination apparatus for determining the location of a first object within a second object.

FIG. 1 shows schematically and exemplarily an embodiment of a location determination apparatus for determining a location of a first object 2 within a second object 3. The location determination apparatus 1 comprises the first object 2, which includes a first ultrasound unit (not shown in FIG. 1), and a second ultrasound unit 5 for being located outside the second object 3, wherein the first ultrasound unit and the second ultrasound 5 are adapted to transmit ultrasound signals between them. The location determination apparatus 1 further comprises a control and processing unit 40 for controlling the location determination apparatus 1 and processing ultrasound information received from the first and second ultrasound units. In particular, the control and processing unit 40 includes a location determination unit 6 for determining the location of the first object 2 within the second object 3 based on the transmitted ultrasound signals.

In this embodiment, the first object 2 is a tip of a catheter 20, which is arranged within a heart 3, which is the second object, of a person 21. The person 21 is located on a table 22.

Figure 2:
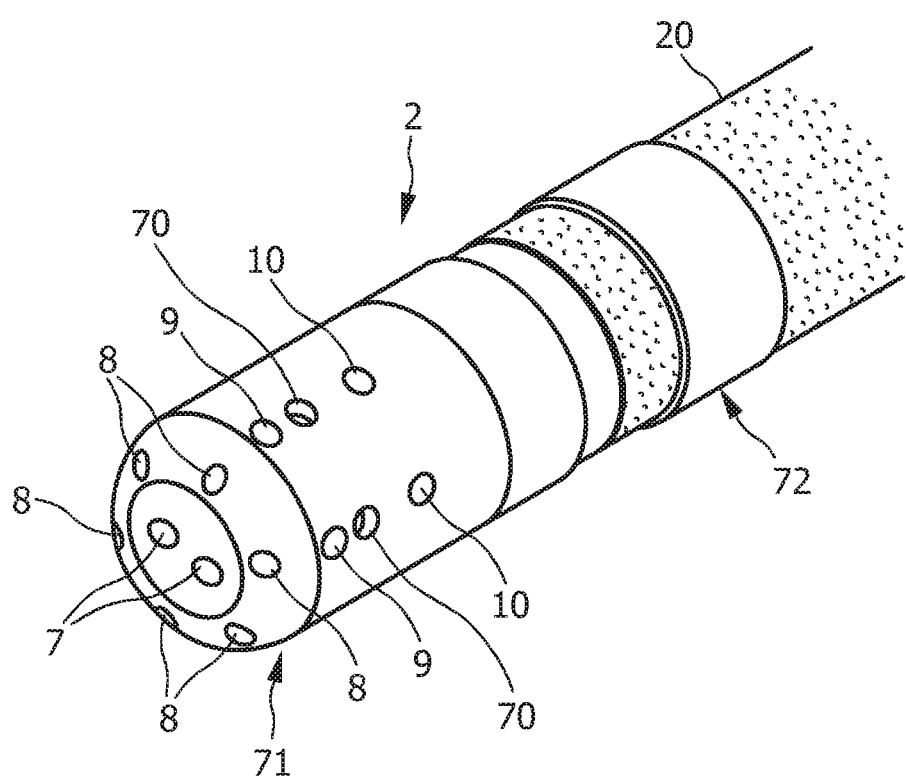
FIG. 2 shows schematically and exemplarily an embodiment of a catheter tip.

The catheter tip 2 is exemplarily shown in more detail in FIG. 2. As can be seen in FIG. 2, the catheter tip 2 comprises several groups 7 . . . 10 of ultrasound transducers forming the first ultrasound unit. The ultrasound units are located on the surface of the catheter tip 2. However, they can also be incorporated within the catheter tip and send and/or receive ultrasound signals through openings in the catheter tip. In particular, the catheter tip 2 can comprise a first group of inner frontal ultrasound transducers 7, a second group of ultrasound transducers 8 circularly arranged around the first group of transducers, and a third group of transducers 9 arranged with a smaller distance to the end of the catheter tip 2 than a fourth group of ultrasound transducers 10 having a larger distance to the end of the catheter tip 2, wherein the third and fourth groups of transducers 9, 10 are located at a side surface of the catheter tip 102. The several ultrasound transducers can be adapted to emit ultrasound at the same frequency or at different frequencies. For example, the ultrasound transducers of a same group can emit ultrasound signals at the same frequency and ultrasound transducers of different groups can emit ultrasound signals at different frequencies, wherein adjacent frequencies are separated by at least the sum of half of the bandwidth of the ultrasound transducers with the adjacent frequencies. The several ultrasound transducers can also be adapted such that each ultrasound transducer emits ultrasound at a different frequency.

The positions of the ultrasound transducers of the first ultrasound unit are known with respect to the catheter tip 2. The location determination unit 6 can therefore be adapted to determine the orientation of the catheter tip 2 based on the transmitted ultrasound signals and the positions of the several ultrasound transducers of the first ultrasound unit, which are known with respect to the catheter tip 2. In particular, the location determination unit 6 can be adapted to determine first positions being the positions of the several ultrasound transducers on the catheter tip 2 with respect to the second ultrasound unit 5 and to determine the orientation of the catheter tip 2 with respect to the second ultrasound unit 5 based on the determined first positions and second positions being the positions of the several ultrasound transducers of the first ultrasound unit, which are known with respect to the catheter tip 2. The location determination unit 6 can therefore be adapted to determine not only the position, but also the orientation of the catheter tip 102.

If the second ultrasound unit 5 receives an ultrasound wave, it can be determined which ultrasound transducer of the first ultrasound unit has sent the ultrasound wave by at least one of the following ways. For example, different ultrasound transducers of the first ultrasound unit can be operated at different frequencies, in order to allow the second ultrasound unit 5 to determine which ultrasound transducer of the first ultrasound unit has sent the respective ultrasound wave based on the frequency of the ultrasound wave. The ultrasound transducers of the first ultrasound unit can also be operated temporally consecutively such that only one ultrasound transducer of the first ultrasound unit is activated at a time, in order to determine which ultrasound transducer of the first ultrasound unit has sent the ultrasound wave based on the time. The ultrasound transducers of the first ultrasound unit can also be operated at the same frequency and at the same time, but with different activation patterns. An activation pattern defines the pulse train waveform, in particular, the number of pulses per cycle and/or the distances between pulses, wherein the pulse train waveform can be different for different ultrasound transducers of the first ultrasound unit. It can then be determined which ultrasound unit has sent which received ultrasound wave depending on the respective pulse train waveform by, for example, performing a correlation analysis which correlates the received ultrasound waves with the known activation patterns of the different ultrasound transducers of the first ultrasound unit.

The ultrasound transducers of the first ultrasound unit can be operated such that ultrasound waves of each individual ultrasound transducer can be discriminated from ultrasound waves of the other ultrasound transducers of the first ultrasound unit or such that ultrasound waves of a group of ultrasound transducers of the first ultrasound unit can be discriminated from ultrasound waves of other groups of ultrasound transducers of the first ultrasound unit.

The second ultrasound unit 5 comprises preferentially one or several two- or three-dimensional ultrasound transducers for receiving the ultrasound signals emitted by the ultrasound transducers located at the catheter tip 2. In this embodiment, the second ultrasound unit 5 comprises a three-dimensional TTE ultrasound transducer, which is arranged on the outer thorax, in particular, placed between the ribs of the person 21. In other embodiments, the one or several two- or three-dimensional ultrasound transducers of the second ultrasound unit can also have another shape and/or size. For example, the second ultrasound unit can also comprise a three-dimensional NOT ultrasound transducer, which is generally used for three-dimensional TTE. A second ultrasound unit 5 comprising a three-dimensional TTE ultrasound transducer, is exemplarily and schematically shown in FIG. 3.

Figure 3:
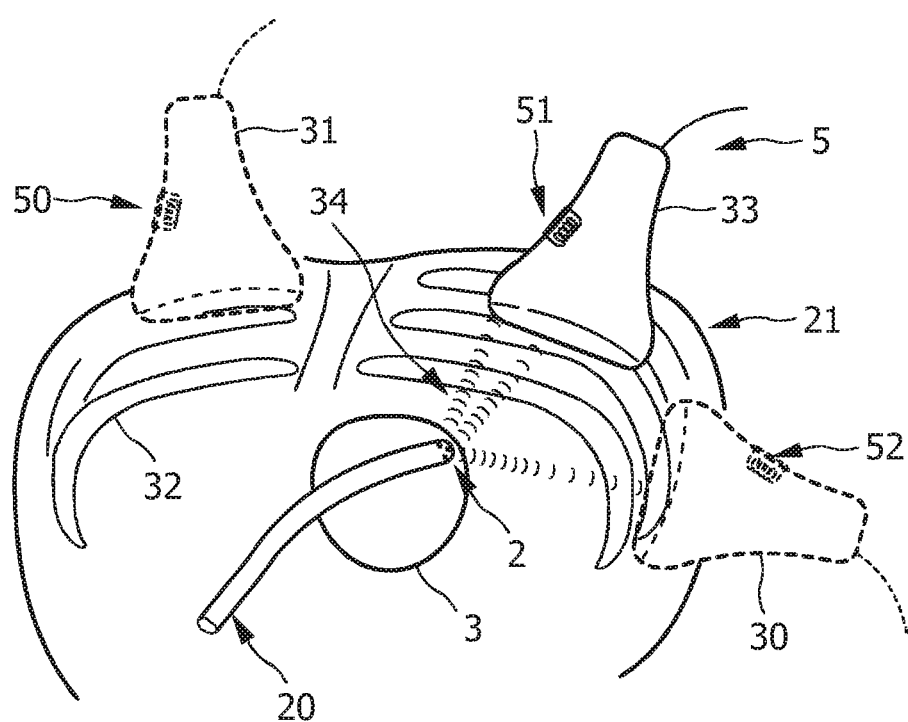
FIG. 3 shows schematically and exemplarily an arrangement of ultrasound transducers on a thorax of a person, which communicate with ultrasound transducers within a heart of a person.

FIG. 3 shows the thorax of the person 21 with ribs 32. A three-dimensional TTE ultrasound transducer 33 of the second ultrasound unit 5 is placed between ribs 32 and receives ultrasound signals 34 from ultrasound transducers located at the catheter tip 2 of the catheter 20, wherein the catheter tip 2 is located within the heart 3. FIG. 3 shows optional further three-dimensional TTE ultrasound transducers 30, 31 of the second ultrasound unit 5 in broken lines, which may also be placed on the thorax of the person 21 between the ribs 32. Also these further optional ultrasound transducers 30, 31 can be used for receiving ultrasound signals from the ultrasound transducers at the catheter tip 2, wherein also these received ultrasound signals can be used for determining the location of the catheter tip 2 within the heart 3.

The location determination unit 6 is adapted to determine the location of the catheter tip 2 within the heart 3 based on at least one of the time of flight and the transmission direction of the transmitted ultrasound signals, i.e. the direction in which the ultrasound signals are emitted and/or received. For example, the position of the catheter tip 2 can be determined by the time of flight and a directionality of the several transducers on the catheter tip 2 with respect to the second ultrasound unit 5 outside of the heart 3. In an embodiment, trilateration and/or one-way beamforming can be used to determine the three-dimensional position and orientation of the catheter tip 2. The location determination unit 6 can also be adapted to determine the orientation of the catheter tip 2 within the heart 3 based on the knowledge from which groups of ultrasound transducers of the first ultrasound unit ultrasound waves can be received by the second ultrasound unit in which orientations, wherein the location determination 106 can comprise a data base in which this knowledge is stored. For example, if the catheter tip 2 is in a perpendicular orientation with respect to the second ultrasound unit, only ultrasound waves from ultrasound transducers of the first and second groups 7 and 8 may be receivable by the second ultrasound unit. Thus, the location determination unit 6 can be adapted to determine that the catheter tip 2 is perpendicular with respect to the second ultrasound unit, if only signals from the first and second groups 7 and 8 are received by the second ultrasound unit. The catheter tip 2 is regarded as being in a perpendicular orientation with respect to the second ultrasound unit, if, for example, the first and second groups 7 and 8 are substantially directed towards the second ultrasound unit such that the ultrasound transducers of the third and fourth groups 9 and 10 emit ultrasound waves in a direction being substantially parallel to a detection surface of the second ultrasound unit.

The catheter tip 2 comprises a cap electrode 71 and a ring electrode 72. The cap electrode 71 comprises the ultrasound transducers of the first ultrasound unit and optional openings 70. The openings 70 can be used, for example, for irrigation purposes. The cap electrode 71 can be used as an ablation electrode for ablating the cardiac tissue by delivering RF energy. The ring electrode 72 and also the cap electrode 71 can also be used as sensing electrodes for picking up electrical activation signals. The electrical activation signals are preferentially electrogram recordings, which may be unipolar recordings or bipolar recordings between the electrode cap 71 and the ring electrode 72. Thus, the cap electrode 71 is preferentially used as an ablation electrode and as a sensing electrode, whereas the ring electrode 72 is preferentially only used as a sensing electrode. The sensing electrode is preferentially used for picking up electrical activation signals at a location that has been determined by the location determination unit 6.

The control and processing unit 40 further comprises a map determination unit 14 for determining an electroanatomic map based on the determined locations of the catheter tip 2 within the heart 3 and the electrical activation signals measured at the determined locations. The catheter tip 2 can be moved to different positions on the heart wall, wherein the different positions can be determined by the location determination unit 6 and wherein electrical activation signals can be measured at these locations by the sensing electrode and used to generate the electroanatomic map.

The ablation electrode 71 is preferentially used to ablate the heart at a location that has been determined by the location determination unit 6, wherein the map determination unit 14 is preferentially adapted to indicate in the electroanatomic map the positions, at which energy has been applied, in particular, at which cardiac tissue has been ablated. The map is therefore a combined map showing positions, at which energy has been applied, and positions, at which the electrical activation signals have been picked up. The map determination unit 14 can further be adapted to show positions, at which energy is planned to be applied. Thus, firstly an electroanatomic map can be generated. Then, a user can indicate positions in the electroanatomic map, which should be ablated, based on the electrical activation shown in the electroanatomic map, wherein the catheter tip 2 can be moved to the positions, which should be ablated. While moving to a desired position, the location of the catheter tip 2 can be determined, in particular, in real-time. After an ablation procedure has been performed at a position, this position can be marked as an ablated position in the electroanatomic map.

The control and processing unit 40 further comprises an ablation depth determination unit 19 for determining the ablation depth based on an ultrasound signal received from at least one of the ultrasound transducers of the catheter tip 2. Thus, at least one of the ultrasound transducers of the catheter tip 2 can be used for sending ultrasound waves out into the cardiac tissue and for receiving reflected ultrasound waves from the cardiac tissue, in order to generate an ultrasound signal, which can be used by the ablation depth determination unit 19 for determining the ablation depth, i.e. for determining a lesion boundary between a lesion generated by the ablation procedure and non-ablated tissue. For example, in an embodiment the first group 7 of ultrasound transducers shown in FIG. 2 may be used for monitoring the ablation depth, whereas the other ultrasound transducers of the catheter tip may be used for determining the location of the catheter tip 2. In another embodiment, a same ultrasound transducer can be used for monitoring the ablation depth and for determining the location of the catheter tip 2, wherein the control and processing unit 40 may be switchable between a first mode, in which the respective ultrasound transducer is used for determining the ablation depth, and a second mode, in which the respective ultrasound transducer is used for determining the location of the catheter tip 2. The determined ablation depth can be shown on a display 17. For example, a ratio of ablated and non-ablated cardiac tissue in depth direction within a wall of the heart can be shown to a user on the display 17 and/or the ultrasound signal used for determining the ablation depth, which is preferentially an M-mode image of the cardiac tissue, may be shown on the display 17 together with an indication like a line indicating the ablation depth within the cardiac tissue. The ablation depth can be shown in real-time on the display 17, in order to allow a user to control an ablation procedure based on the determined ablation depth. For more details regarding a determination of the ablation depth depending on ultrasound reference is made to WO 2010/082146 A1, which is herewith incorporated by reference.

The ultrasound transducers at the catheter tip 2, which are used for determining the ablation depth, have preferentially a frequency within the range of 20 MHz to 40 MHz. Moreover, these ultrasound transducers have preferentially a relatively large bandwidth, which is, for example, larger than 30%. The ultrasound transducers at the catheter tip 2, which are used for determining the location of the catheter tip, have preferentially a frequency within the range of 1 and 10 MHz and a relatively small bandwidth of, for example, 10% or smaller.

If an ultrasound transducer, which is located at the catheter tip 2, is used for determining the ablation depth and for locating the catheter tip, the respective ultrasound transducer is preferentially tunable, i.e. the frequency of the respective ultrasound transducer is preferentially modifiable. In particular, the respective ultrasound transducer is preferentially controllable such that for determining the location of the catheter tip 2 the respective ultrasound transducer is operated at a frequency being lower than the frequency used for monitoring the ablation depth. For instance, for determining the location of the catheter tip 2, the respective ultrasound transducer is operated at a frequency within the range of 1 and 10 MHz and for determining the ablation depth the respective ultrasound transducer is operated at a frequency between 20 MHz and 40 MHz.

Figure 4:
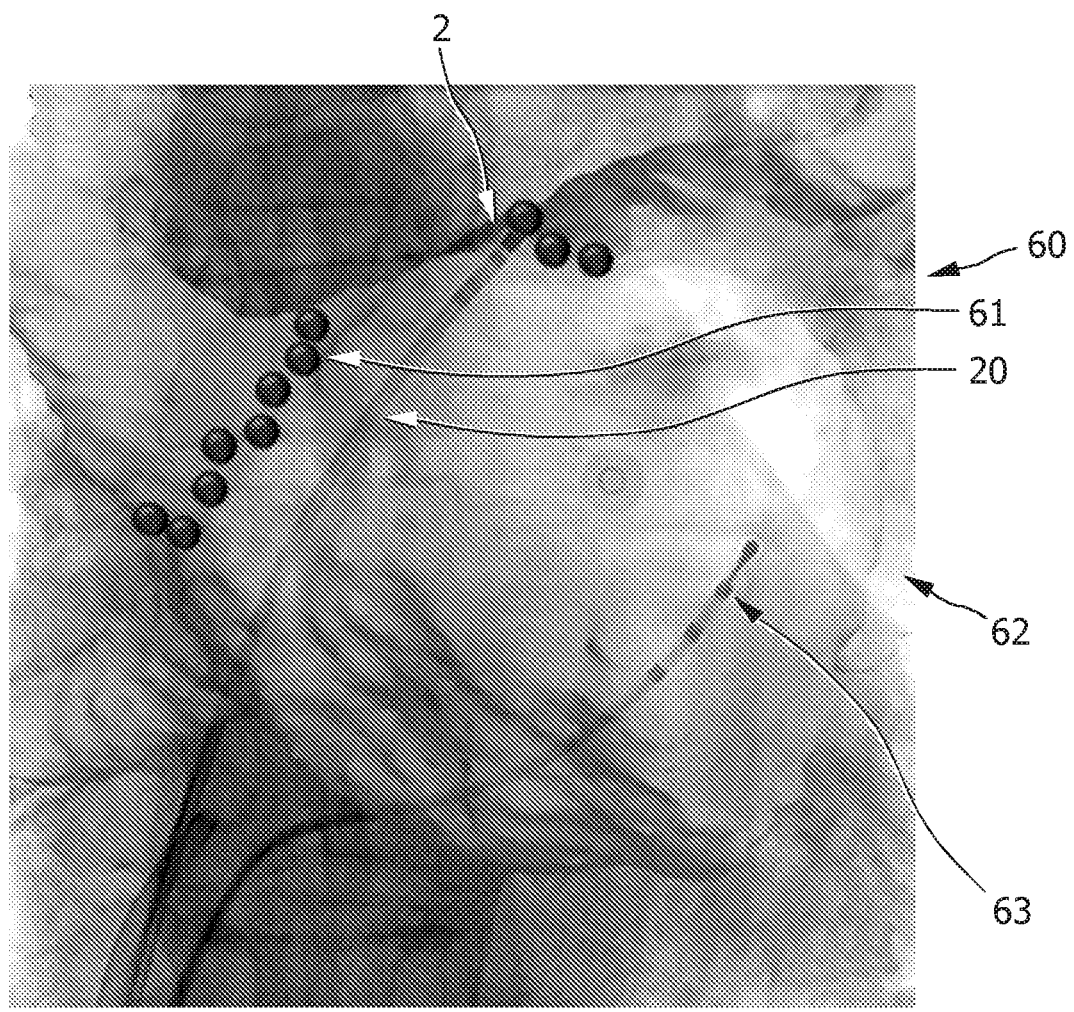
FIG. 4 shows schematically and exemplarily an electroanatomic map with planned ablation positions.

FIG. 4 shows schematically and exemplarily an electroanatomic map 62. The electroanatomic map 62 comprises dots 61, which indicate planned ablation positions. In the example shown in FIG. 4, the tip 2 of the catheter 20 is located at a planned ablation position for ablating the cardiac tissue at this position. Optionally, a further diagnostic catheter 63 can be used for measuring local electrograms. However, this further diagnostic catheter is not necessary and can be omitted.

Figure 5:
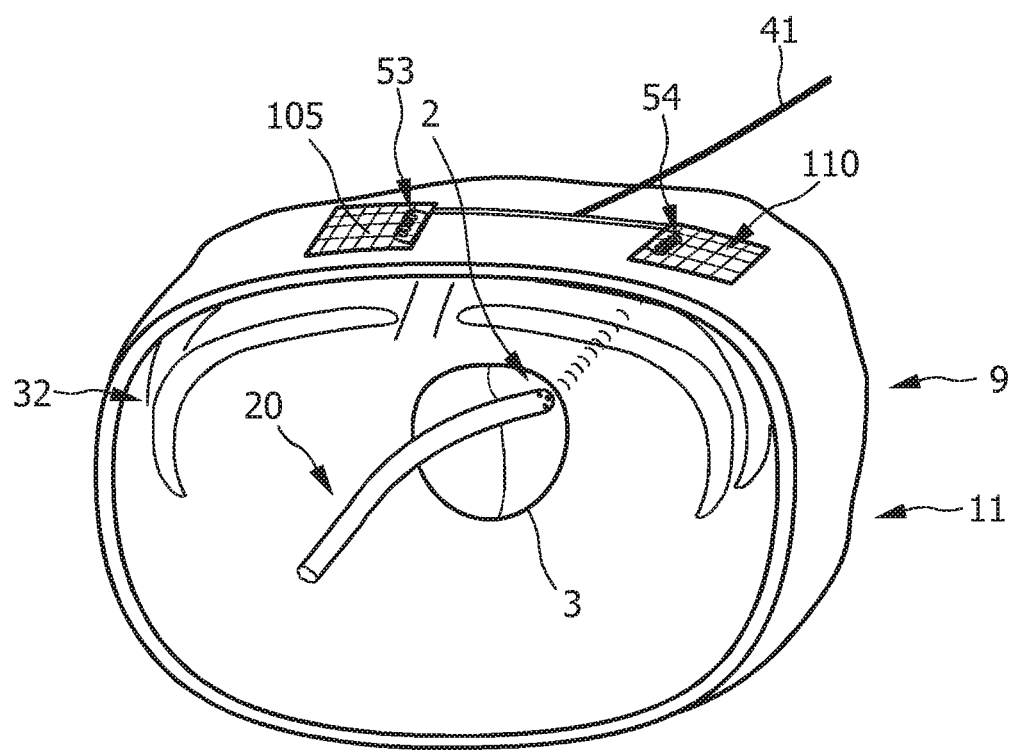
FIG. 5 shows schematically and exemplarily a vest worn by a person in which ultrasound transducers are integrated, which communicate with ultrasound transducers within a heart of a person.

In an embodiment, the location determination apparatus can comprise a fixation arrangement for fixing the second ultrasound unit on the person 11 as schematically and exemplarily shown in FIG. 5.

FIG. 5 shows schematically and exemplarily a cross-section of the thorax 11 with ribs 32 and the heart 3. The catheter 20 with the catheter tip 2 has been introduced into the heart 3. The catheter tip 2 comprises the first ultrasound unit, wherein ultrasound signals are transmitted between the first ultrasound unit and ultrasound transducers 105, 110 arranged on the thorax 11 of the person 21. The ultrasound transducers 105, 110 form, in this embodiment, the second ultrasound unit 5, which is fixed on the thorax 11 of the person 21 by using a fixation arrangement being a vest 9.

In an embodiment, the control and processing unit 40, in particular, a sub-control unit 13 of the control and processing unit 40, can be adapted such that, before determining the location of the catheter tip 2, the ultrasound transducers of the second ultrasound unit 5 are operated for generating ultrasound signals showing the thorax 11. The control and processing unit 40 can then further be adapted to determine which part of the ultrasound transducers has received a reflected ultrasound wave from a rib 32, in order to determine which part of the ultrasound transducers is arranged on a rib 32 of the thorax 11. During the determination of the location of the catheter tip 2 then preferentially only the parts of the ultrasound transducers of the second ultrasound unit 5 are operated, which are not located on a rib 32 of the thorax 11, i.e. only parts of the ultrasound transducers of the second ultrasound unit 5 are used, which fall intercostal.

The location determination apparatus 1 further comprises a second ultrasound unit position determination unit 12 for determining the position of the second ultrasound unit 5 with respect to a reference coordinate system, wherein the location determination unit 6 is adapted to determine the position of the catheter tip 2 within the heart 3 with respect to the reference coordinate system based on the transmitted ultrasound signals and the determined position of the second ultrasound unit 5 with respect to the reference coordinate system. This allows accurately positioning the catheter tip 2 within the heart 3, even if the second ultrasound unit 5, in particular, the ultrasound transducers of the second ultrasound unit 5, changes the position during the positioning procedure.

The position determination unit 12 communicates with position sensors on the second ultrasound unit, in particular, on the ultrasound transducers of the second ultrasound unit, which are schematically and exemplarily shown in the embodiments illustrated in FIGS. 3 and 5. In FIGS. 3 and 5, these position sensors are denoted by 50 . . . 54. The position sensors 50 . . . 54 are EM sensors, which communicate with the second ultrasound unit position determination unit 12 for determining the three-dimensional position of the ultrasound transducers of the second ultrasound unit 5. In other embodiments, other position sensors like optical position sensors can be used for determining the three-dimensional position of the ultrasound transducers of the second ultrasound unit. By determining the positions of the ultrasound transducers of the second ultrasound unit with respect to a common reference coordinate system, the ultrasound transducers of the second ultrasound unit can be registered with respect to each other. This can lead to a larger aperture consisting of a union of apertures of all ultrasound transducers of the second ultrasound unit for performing a tracking of the catheter tip, in particular, of determining the location and orientation of the catheter tip, thus achieving better accuracy or, at least, better robustness of tracking.

The control and processing unit 40 further comprises an ultrasound image generation unit 15 for generating an ultrasound image of the heart 3 based on ultrasound information from the second ultrasound unit 5, wherein the location determination unit 6 can be adapted to determine the location of the catheter tip 2 within the heart 3 with respect to the ultrasound image based on the ultrasound signals transmitted between the first and second ultrasound units and the ultrasound information received from the second ultrasound unit 5.

The control and processing unit 40 further comprises a registration unit 16 for registering the ultrasound image with a previously acquired image or a model of the heart 3, wherein the location determination unit 6 is adapted to determine the location of the catheter tip 2 within the heart 3 based on the determined location with respect to the ultrasound image and the registration result. The ultrasound image of the heart is preferentially a currently acquired three-dimensional ultrasound image and the previously acquired image is preferentially a previously acquired three-dimensional ultrasound image or a three-dimensional image of another imaging modality like a computed tomography image, a magnetic resonance image, et cetera. The model is preferentially also three-dimensional.

In particular, the location determination unit 6 can determine the location of the catheter tip 2 within the heart 3 with respect to the second ultrasound unit 5 depending on the ultrasound signals transmitted between the first ultrasound unit comprised by the catheter tip 2 and the second ultrasound unit 5 by using, for example, the time of flight and a directionality of the ultrasound units. Since the location determination unit 6 determines the location of the catheter tip 2 with respect to the second ultrasound unit 5 and since the second ultrasound unit 5 can also be adapted to generate a three-dimensional image of the heart 3, the location of the catheter tip 2 within the ultrasound image of the heart is known. By registering this ultrasound image with a previously acquired three-dimensional image or a three-dimensional model, the location of the catheter tip 2 is determined with respect to the previously acquired image or the model.

Figure 6:
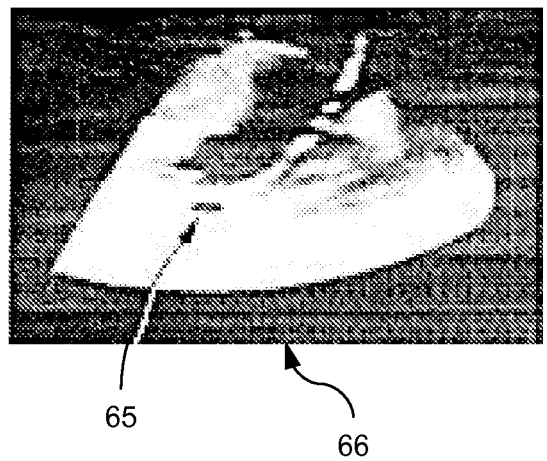
FIG. 6 shows schematically and exemplarily an ultrasound image overlaid with a determined location of a catheter tip.

In order to visualize the location of the catheter tip 2 within the heart 3 with respect to the ultrasound image based on the ultrasound signals transmitted between the first and second ultrasound units and the imaging ultrasound information received from the second ultrasound unit 5, the location determination unit 6 can be adapted to generate an image showing only a colored or white spot, which indicates the location of the catheter tip 2 within the heart 3 determined by using the ultrasound signals transmitted between the first and second ultrasound units, against a dark background and to overlay this bright spot with the dark background with the ultrasound image generated by the ultrasound image generation unit 15 based on the ultrasound imaging performed by the second ultrasound unit 5. A corresponding overlay image is schematically and exemplarily shown in FIG. 6. In FIG. 6, the colored spot 65, which indicates the location of the catheter tip 2, is shown overlaid on an actual ultrasound image 66.

The sub-control unit 13 can be adapted to control the catheter, in particular, the sensing and ablation electrodes and the navigation of the catheter tip, and the first and second ultrasound units. In particular, the sub-control unit 13 can be adapted to receive ultrasound information for imaging and for determining the location of the catheter tip 2 within the heart 3 from the first and second ultrasound units via a data connection 41 like an electrical and/or optical connection, for example, a cable, and for providing this ultrasound information to, for example, the location determination unit 6 and the ultrasound image generation unit 15. The generated images like the mentioned overlay images and/or the electroanatomic map can be shown on the display 17.

Figure 7:
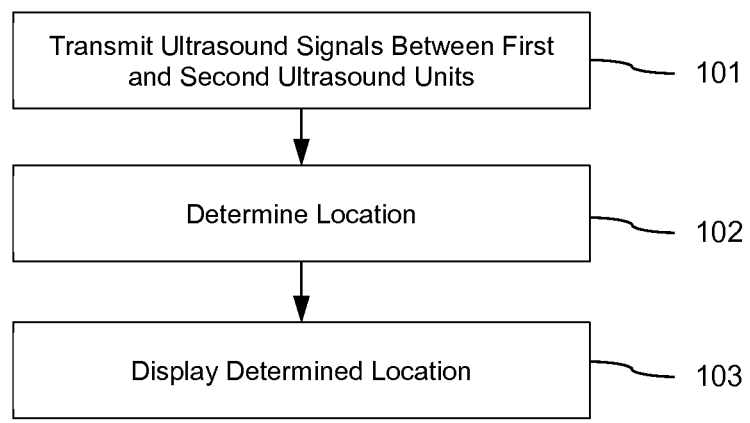
FIG. 7 shows a flowchart exemplarily illustrating an embodiment of a location determination method for determining a location of a first object within a second object.

In the following an embodiment of a location determination method will exemplarily be described with reference to a flowchart shown in FIG. 7.

In step 101, ultrasound signals are transmitted between a first ultrasound unit located on the catheter tip 2, which has been inserted into the heart 3 of the person 21, and a second ultrasound unit 5 located outside of the heart 3 of the person 21. Preferentially, the second ultrasound unit 5 is arranged on the thorax of the person 21. In step 102, the location of the catheter tip 2 within the heart 3 is determined based on the ultrasound signals transmitted between the first and second ultrasound units by using, for example, the time of flight and/or a directionality of the ultrasound units. In step 103, the determined location of the catheter tip 2 is shown on the display 17.

Figure 8:
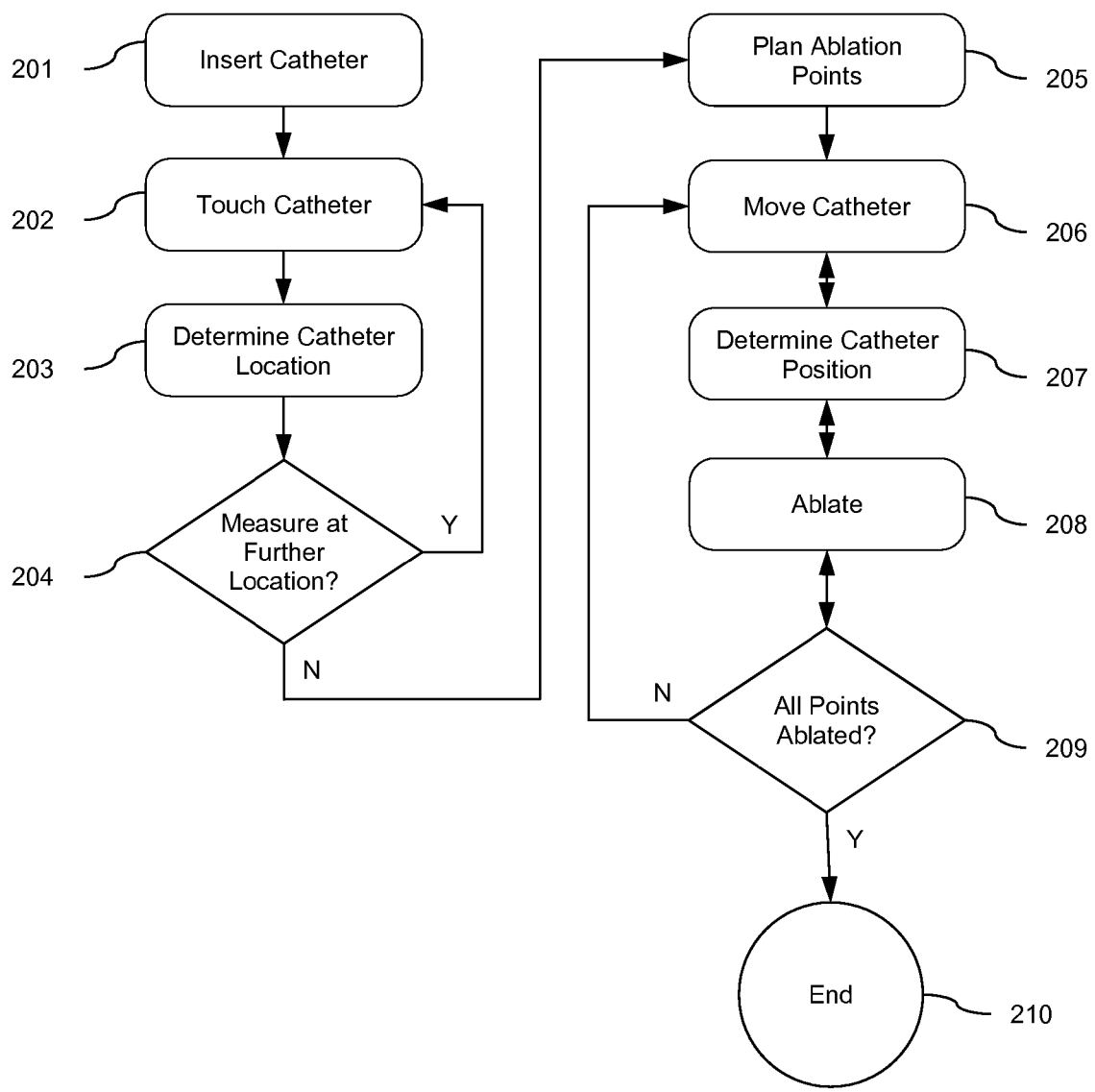
FIG. 8 shows a flowchart exemplarily illustrating a workflow of a process of applying the substance determination apparatus.

In the following, a preferred use of the location determination apparatus 1 will exemplarily be described with reference to the workflow shown in FIG. 8.

In step 201, the catheter 20 is inserted into the heart 3 of the person 21, and, in step 202, the catheter tip is moved to touch the surface of the heart 3. In step 203, the current location of the catheter tip 2 is determined, the electrical activity is measured at the determined location, and a three-dimensional ultrasound image is generated by using the second ultrasound unit 5. The determined location of the catheter tip 2, the measured electrical activity and the three-dimensional ultrasound image are saved. In step 204, it is decided, for example, by a user, whether the electrical activity should be measured at a further location or not. If the electrical activity should be measured at a further location, the catheter tip is moved to another position at the surface of the heart 3 (step 202) and the workflow continues at this new position with step 203. If it has been decided to stop the repetition of steps 202 to 204, the stored locations and measured electrical activities are used for generating an electroanatomic map of the heart 3, and, in step 205, ablation points, at which the heart 3 should be ablated, are planned based on the electroanatomic map.

In step 206, the catheter tip is moved to a desired planned ablation position, while during the movement the location determination unit 6 determines the position of the catheter tip 2 in a currently acquired three-dimensional ultrasound image (step 207). If the desired location has been reached, the cardiac tissue is ablated at this location in step 208. Also during the ablation procedure the location of the catheter tip 2 can be determined and shown in a currently acquired three-dimensional ultrasound image on the display 17. Moreover, while applying the ablation energy the ablation depth can be determined in real-time for controlling the ablation procedure depending on the determined ablation depth. In step 209, it is checked, whether all desired points have been ablated. If this is not the case, the workflow continues with step 206. If all points have been ablated, the workflow ends in step 210.

In step 205, ablation points, at which the heart 3 should be ablated, can also be planned based on a three-dimensional ultrasound image of the heart 3, which only provides anatomic information. For example, if an isolation of pulmonary veins is desired, corresponding ablation points may be planned based on the anatomic information provided by the three-dimensional ultrasound image. In addition of alternatively, for example, sites of early activation could be planned based on the electroanatomic map.

In step 203, the generation of the three-dimensional ultrasound image and the saving of the generated three-dimensional ultrasound image are optional, i.e. in steps 202 to 204 the electroanatomic map can also be determined without generating and saving a three-dimensional ultrasound image.

During carrying out the workflow, the respective location of the catheter tip 2, which has been determined based on the ultrasound signals transmitted between the first and second ultrasound units, can be shown on a currently acquired three-dimensional ultrasound image and/or in a previously acquired three-dimensional image, which may be an ultrasound image or an image of another imaging modality. The determined location of the catheter tip 2 can also be shown in a model of the heart 3. In order to show the determined location of the catheter tip 2 in a pre-acquired three-dimensional image or in a model of the heart 3, the currently acquired three-dimensional ultrasound image is preferentially registered with the pre-acquired image and/or the model as described above. The registration can be performed by using, for example, known segmentation techniques as performed by, for instance, the EP Navigator of the company Philips. Moreover, the position of the second ultrasound unit provided by the second ultrasound unit position determination unit 12 can be used for registering the currently acquired three-dimensional ultrasound image with a pre-acquired image and/or the model. In particular, since the orientation and position of the currently acquired three-dimensional ultrasound image with respect to the second ultrasound unit is known, because, for example, the three-dimensional ultrasound image has been acquired by using the second ultrasound unit, and by knowing the three-dimensional position of the second ultrasound unit with respect to a reference coordinate system, in which also the position of the pre-acquired image and/or the model is known, the currently acquired three-dimensional ultrasound image can be registered with the pre-acquired image and/or the model. The second ultrasound unit position determination unit uses, for example, electromagnetic or fiber optics based tracking, in order to determine the position of the second ultrasound unit with respect to the reference coordinate system. Fiber optics based tracking can be based on, for example, Rayleigh scattering or fibers with integrated Bragg gratings.

The location determination apparatus and method are preferentially adapted to perform cardiac mapping, wherein temporal and spatial distributions of myocardial electrical potentials are identified during a particular heart rhythm. In particular, the location determination apparatus and method can be adapted to perform electroanatomical mapping (EAM), wherein a three-dimensional location of a mapping catheter can be determined with local electrograms to reconstruct in real-time a representation of the three-dimensional geometry of the heart chamber color-coded with relevant electrophysiological information. The reconstruction of the representation of the three-dimensional geometry of the heart chamber can be achieved by choosing the anatomy provided by the three-dimensional ultrasound image acquired in real-time. In addition, the location determination apparatus and method can be adapted to tag anatomic landmarks and ablation lesions to facilitate mapping and ablation. Preferentially, they reliably allow catheter positioning without fluoroscopy. The generated EAM can be used, for example, to facilitate pulmonary vein isolation for treatment for atrial fibrillation.

Although, in the above described embodiments, the second object is a heart of a person, in other embodiments the second object can also be another object like another part of a person or of an animal, for example another organ or a blood vessel. The second object can also be a technical object.

Although in the above described embodiments an electroanatomic map of the heart is determined, in other embodiments the sensing of properties of the second object, in particular, the measurement of the electrical activity of the heart at different locations, may not be present. For example, the catheter tip can just be moved to different positions within the heart, at which the catheter tip touches the heart wall, and at these positions the three-dimensional locations of the catheter tip can be determined for generating an anatomic map, which does not comprise, for example, electrical information. An anatomic map can be used, for example, for a purely anatomical ablation like a paroxysmal AF treatment.

Although, in the above described embodiments, the catheter tip is adapted to apply electrical energy, in particular, RF energy, to the cardiac tissue, the catheter tip can also be adapted to apply other kinds of ablation energy to the cardiac tissue like optical energy provided by a laser via optical fibers arranged within the catheter.

Although in the above described embodiments catheters with certain catheter tips are exemplarily described, the catheter can also comprise another kind of catheter tip like a multipoint ablation catheter tip or a balloon-type catheter tip.

The generated electroanatomic map can be registered with life-fluoro- and/or pre-procedural data like computed tomography or magnetic resonance images by using segmentation techniques. Another possibility to register the electroanatomic map with life-fluoro- and/or pre-procedural data is to use the position sensor, which may be attached to the second ultrasound unit as described above.

The location determination apparatus and method are preferentially adapted to be used in applications for treating heart arrhythmia and/or other applications, in particular, applications in which a purely anatomic map or electroanatomic map based navigation is performed.

Although in the above described embodiments, the first object is preferentially a catheter tip, in other embodiments the first object can also be another object, in particular, another in-body device like a needle.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Calculations like the determination of the location of the first object and the determination of the ablation depth, and the control of parts of the location determination apparatus or of the entire location determination apparatus performed by one or several units or devices can be performed by any other number of units or devices. The calculations and/or the control of parts of the location determination apparatus or of the entire location determination apparatus in accordance with the location determination method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication system.

Any reference signs in the claims should not be construed as limiting the scope.

The invention relates to location determination apparatus for determining a location of a first object like a catheter within a second object being, for example, the heart of a person. The first object comprises a first ultrasound unit, and a second ultrasound unit is located outside the second object. A location determination unit determines the location of the first object within the second object based on ultrasound signals transmitted between the first ultrasound unit and the second ultrasound unit. This allows determining the location of the first object within the second object reliably in a way which is an alternative to using a transmission of electrical signals for determining the location and which may lead to an improved accuracy of determining the location.

The invention claimed is:

1. A location determination apparatus for determining a location of a first ultrasound unit within an object (3), wherein the location determination apparatus (1) comprises:
the first ultrasound unit comprising at least one ultrasound transducer,
a second ultrasound unit (5) comprising at least one ultrasound transducer for being located outside the object (3), wherein the at least one ultrasound transducer of the first ultrasound unit and the at least one ultrasound transducer of the second ultrasound unit (5) are adapted to transmit ultrasound signals between them,
an ultrasound image generation unit (15) for generating an ultrasound image of the object (3) based on ultrasound information from at least one of the at least one ultrasound transducer of the first ultrasound unit (7, 8, 9, 10) and the at least one ultrasound transducer of the second ultrasound unit (5; 105, 110),
a location determination unit (6) for determining the location of the first ultrasound unit within the object (3) with respect to the ultrasound image based on the ultrasound signals transmitted between the at least one ultrasound transducer of the first ultrasound unit and the at least one ultrasound transducer of the second ultrasound unit and the ultrasound information from at least one of the first ultrasound unit and the second ultrasound unit.

2. The location determination apparatus as defined in claim 1, wherein at least one of the first ultrasound unit and the second ultrasound unit (5) comprises several ultrasound transducers (7, 8, 9, 10) for transmitting ultrasound signals between the first and second ultrasound units and wherein the several ultrasound transducers (7, 8, 9, 10) emit ultrasound signals at the same or at different frequencies.

3. The location determination apparatus as defined in claim 2, wherein the first ultrasound unit is located on a catheter tip and comprises several ultrasound transducers (7, 8, 9, 10) arranged at positions on or within the catheter tip, which are known with respect to the first catheter tip, wherein the several ultrasound transducers (7, 8, 9, 10) emit or receive ultrasound signals at different frequencies, and wherein the location determination unit (6) is adapted to determine the orientation of the catheter tip based on the transmitted ultrasound signals and the positions of the several ultrasound transducers (7, 8, 9, 10), which are known with respect to the catheter tip.

4. The location determination apparatus as defined in claim 1, wherein the location determination unit (6) is adapted to determine the location of the first ultrasound unit within the object based on at least one of a time of flight and a transmission direction of the transmitted ultrasound signals.

5. The location determination apparatus as defined in claim 1, wherein the first ultrasound unit is adapted to measure a property of the object (3) at the location at which the first ultrasound unit is arranged within the object.

6. The location determination apparatus as defined in claim 5, wherein the location determination apparatus (1) further comprises a map determination unit (14) for determining a property map based on determined locations of the first ultrasound unit within the object (3) and properties of the object (3), which have been measured at the determined locations.

7. The location determination apparatus as defined in claim 1, wherein the first ultrasound unit is associated with an electrode (71) adapted to apply energy to the object (3) at the location at which the first ultrasound unit is arranged within the object (3).

8. The location determination apparatus as defined in claim 1, wherein the location determination apparatus further comprises a fixation arrangement (9) for fixing the second ultrasound unit (105, 110) on a subject (11) in which the object (3) is located.

9. The location determination apparatus as defined in claim 1, wherein the location determination apparatus further comprises a second ultrasound unit position determination unit (12) for determining the position of the second ultrasound unit (5; 105, 110) with respect to a reference coordinate system, wherein the location determination unit (6) is adapted to determine the position of the first ultrasound unit within the object (3) with respect to the reference coordinate system based on the transmitted ultrasound signals and the determined position of the second ultrasound unit (5; 105, 110) with respect to the reference coordinate system.

10. The location determination apparatus as defined in claim 1, wherein the location determination apparatus (1) further comprises a registration unit (16) for registering the ultrasound image with a previously acquired image or a model of the object (3) and wherein the location determination unit (6) is adapted to determine the location of the first ultrasound unit within the object (3) based on the determined location with respect to the ultrasound image and the registration result.

11. A location determination method for determining a location of an ultrasound unit within an object (3), wherein the location determination method comprises:
   transmitting ultrasound signals between at least one ultrasound transducer comprising the first ultrasound unit and at least one ultrasound transducer comprising the second ultrasound unit (5) located outside the object (3),
   generating an ultrasound image of the object (3) based on ultrasound information from at least one of the at least one ultrasound transducer comprising the first ultrasound unit (7, 8, 9, 10) and the at least one ultrasound transducer comprising the second ultrasound unit (5; 105, 110) by an ultrasound image generation unit (15), and
   determining the location of the first ultrasound unit within the object (3) with respect to the ultrasound image based on the ultrasound signals transmitted between the at least one ultrasound transducer comprising the first ultrasound unit and the at least one ultrasound transducer comprising the second ultrasound unit and the ultrasound information from at least one of the at least one ultrasound transducer comprising the first ultrasound unit and the at least one ultrasound transducer comprising the second ultrasound unit by a location determination unit (6).

12. A computer program product comprising a non-transient computer readable storage medium having encoded thereon, program steps for determining the location of a first ultrasound unit within an object, the program steps comprising the steps of:
   transmitting ultrasound signals between the first ultrasound unit comprised by at least one ultrasound transducer and a second ultrasound unit (5) located outside the object (3) comprised by at least one ultrasound transducer,
   generating an ultrasound image of the object (3) based on ultrasound information from at least one of the at least one ultrasound transducer of the first ultrasound unit (7, 8, 9, 10) and the at least one ultrasound transducer of the second ultrasound unit (5; 105, 110) by an ultrasound image generation unit (15), and
   determining the location of the first ultrasound unit within the object (3) with respect to the ultrasound image based on the ultrasound signals transmitted between the at least one ultrasound transducers of the first and second ultrasound units and the ultrasound information from the at least one ultrasound transducers of at least one of the first ultrasound unit and the second ultrasound unit by a location determination unit (6).

* * * * *